United States Patent [19]

Dittrich

[11] Patent Number: 4,609,649
[45] Date of Patent: Sep. 2, 1986

[54] PESTICIDAL COMPOSITIONS EMPLOYING A SYNERGISTIC COMBINATION OF ENDOSULFAN AND PROFENOFOS

[75] Inventor: Volker Dittrich, Zeiningen, Switzerland

[73] Assignee: Ciba-Geigy Corporation, Ardsley, N.Y.

[21] Appl. No.: 757,700

[22] Filed: Jul. 22, 1985

[30] Foreign Application Priority Data

Jul. 31, 1984 [CH] Switzerland .................. 3700/84

[51] Int. Cl.⁴ ............................................. A01N 57/10
[52] U.S. Cl. .................................................. 514/147
[58] Field of Search ........................... 514/431, 147

[56] References Cited

U.S. PATENT DOCUMENTS 3,091,564  5/1963  Frensch et al. .................. 514/431
3,992,533  11/1976  Beriger et al. ................. 514/147
4,103,007  7/1978  Joppien ............................. 514/431

*Primary Examiner*—Allen J. Robinson
*Attorney, Agent, or Firm*—Edward McC. Roberts; Kevin T. Mansfield

[57] ABSTRACT

The present invention relates to a pesticidal composition containing as active component a combination of the compound of the formula

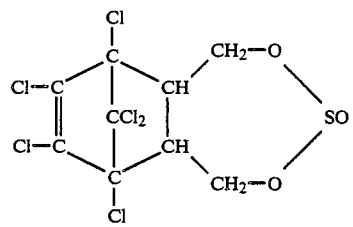

(A)

and the compound of the formula

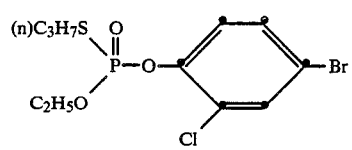

(B)

in a ratio of 1:1 to 1:100, and to the use thereof for controlling various pests of animals and plants.

5 Claims, 1 Drawing Figure

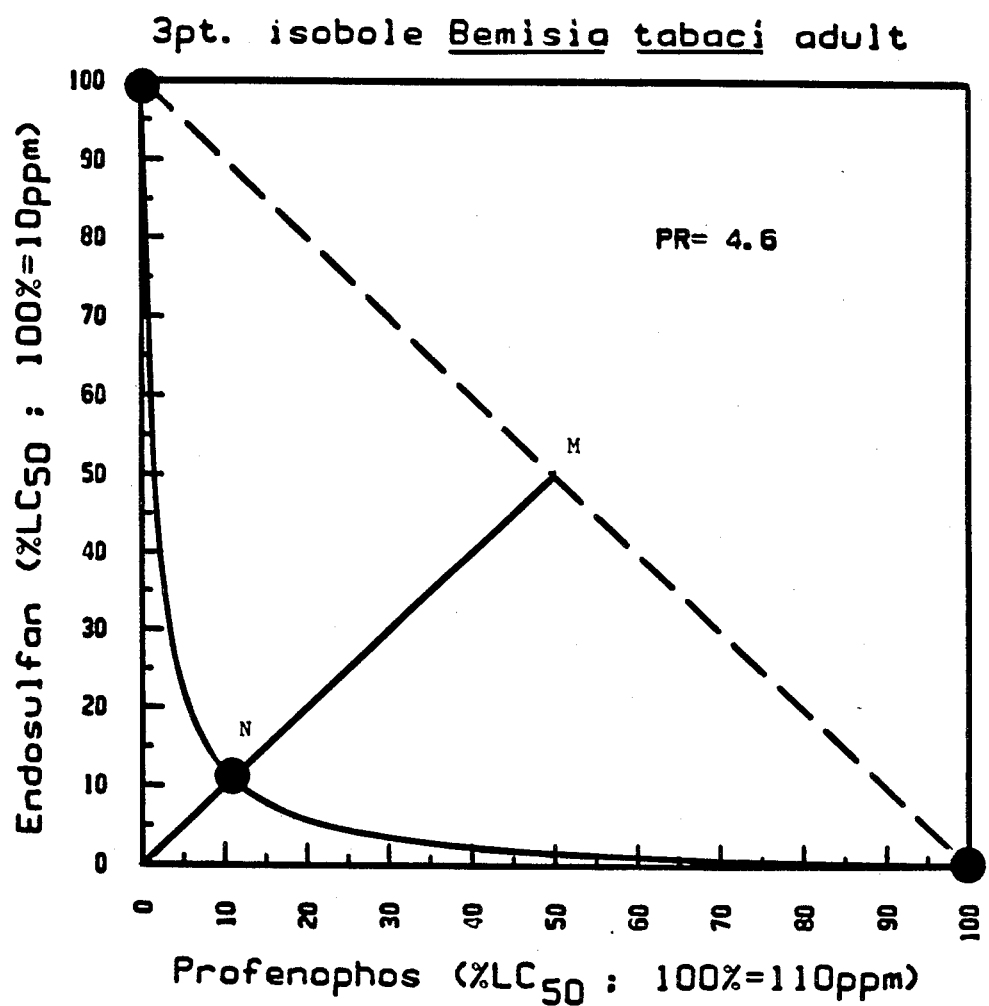

PESTICIDAL COMPOSITIONS EMPLOYING A SYNERGISTIC COMBINATION OF ENDOSULFAN AND PROFENOFOS

The present invention relates to pesticidal compositions which contain as active component a combination of endosulfan, known from U.S. Pat. No. 2,799,685, of the formula

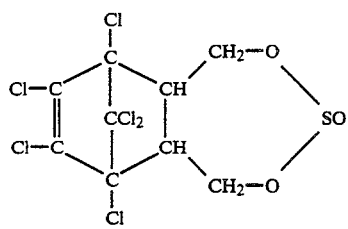

and profenofos of the formula

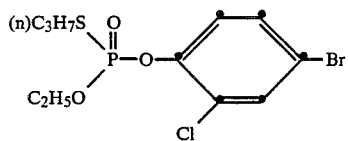

known from German Offenlegungsschrift No. 2 249 462, in a ratio of 1:1 to 1:100, to the use thereof for controlling various pests of animals and plants, as well as to suitable methods of controlling said pests.

Mixtures of substances of different classes, e.g. of formamadines, ureas, carbamates, phosphates and pyrethroids, have already been described as synergistically effective compositions for pest control. However, it has been found that the known compositions containing a combination of active ingredients do not always meet the requirements made of them in practice, especially of effectiveness, toxicity and economy, to the desired degree.

Surprisingly, it has now been found that combinations of pesticides A and B in a ratio of 1:1 to 1:100, preferably 1:9, have a potentiated activity against various pests of animals and plants which by far exceeds the additive activity of these known combinations. The potentiated activity of pesticides A and B against various pests of animals and plants is exhibited in all methods of control. Accordingly, methods may be employed wherein the pesticides A and B are applied to the habitat of the pests either premixed from a single container or separately at brief intervals in succession or simultaneously from different containers.

Combinations of pesticides A and B are particularly suitable for controlling all stages of development of insects, e.g. of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and for controlling mites of the order Acarina, which are parasitic on plants and animals, as well as ticks of the order Acarina.

Combinations of pesticides A and B are most particularly suitable for controlling eating and sucking insects in ornamentals and crops of useful plants. In particular, resistant strains of the white fly (Bemisia tabaci) in crops of cotton can be controlled with these combinations.

The combinations of pesticides A and B are used in known manner, together with the adjuvants conventionally employed in formulation technology, as formulations, e.g. emulsifiable concentrates, suspension concentrates, directly sprayable or dilutable solutions, dilute emulsions, wettable powders, soluble powders, dusts, granulates, and also encapsulations in polymer substances and the like. The methods of application, such as spraying, atomising, dusting, scattering or pouring, are chosen in accordance with the intended uses. Care must be taken that the method of application and the nature and amount of the adjuvants employed for preparing the formulation do not substantially affect the biological properties of the combination of active ingredients.

The formulations are prepared in known manner, e.g. by homogeneously mixing and/or grinding the active ingredients A and B alone or combinations thereof with solvents, solid carriers and, where appropriate, surface-active compounds (surfactants). Suitable solvents are: aromatic hydrocarbons, preferably the fractions containing 8 to 12 carbon atoms, e.g. from mixtures of xylenes up to substituted naphthalenes, aliphatic hydrocarbons such as cyclohexane or paraffins, alcohols and glycols and their ethers and esters, strongly polar solvents such as dimethylsulfoxide or dimethylformamide, as well as water. The solid carriers used e.g. for dusts and dispersible powders, are normally natural mineral fillers. Chemically, particularly suitable solid carriers are calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds are nonionic, cationic and/or anionic surfactants having good emulsifying, dispersing and wetting properties.

Examples of suitable cationic surfactants are quaternary ammonium compounds, e.g. cetyltrimethylammonium bromide. Examples of suitable anionic surfactants are soaps, salts of aliphatic monoesters of sulfuric acid, e.g. sodium lauryl sulfate, salts of sulfonated aromatic compounds, e.g. sodium dodecylbenzenesulfonate, sodium lignosulfonate, calcium lignosulfonate, ammonium lignosulfonate, butyl naphthalenesulfonate and a mixture of the sodium salts of diisopropyl naphthalenesulfonate and triisopropyl naphthalenesulfonate. Examples of suitable non-ionic surfactants are the condensation products of ethylene oxide with fatty alcohols, e.g. oleyl alcohol or cetyl alcohol, or with alkyl phenols, e.g. octyl phenol, nonyl phenol and octyl resol. Other non-ionic compositions are the partial esters which are derived from long-chain fatty acids and hexite anhydrides, the condensation products of said partial esters with ethylene oxide, and the lecithins.

The non-ionic, anionic and cationic surfactants customarily employed in formulation technology are described e.g. in the following publications:

"McCutcheon's Detergents and Emulsifier's Annual", MC Publishing Corp., Ridgewood, N.J., 1979; Dr. Helmet Stache, "TensidTaschenbuch", Carl Hanser Verlag, Munich/Vienna, 1981.

The formulations usually contain 0.1 to 99%, in particular 0.1 to 95%, of a combination of active ingredients A+B (ratio 1:1 to 1:100), 0 to 25% of a surfactant, and 1 to 99.9% of a solid or liquid adjuvant.

The formulations may also contain further auxiliaries such as stabilisers, antifoams, viscosity regulators, binders, tackifiers or also fertilisers for obtaining special effects.

Combinations of pesticides A+B may e.g. be formulated as follows:

FORMULATION EXAMPLES FOR COMBINATIONS OF PESTICIDES A+B (PERCENTAGES ARE BY WEIGHT)

| 1. Emulsifiable concentrates | (a) | (b) | (c) |
|---|---|---|---|
| a combination of A + B | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (36 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| a combination of A + B | 80% | 10% | 5% | 95% |
| ethylene glycol monomethyl ether | 20% | — | — | — |
| polyethylene glycol mol. wt. 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 3. Granulates | (a) | (b) |
|---|---|---|
| a combination of A + B | 5% | 10% |
| kaolin | 94% | — |
| highly dispersed silicic acid | 1% | — |
| attapulgite | — | 90% |

The combination of active ingredients is dissolved in methylene chloride, the solution is sprayed onto the carrier, and the solvent is subsequently evaporated off in vacuo.

| 4. Dusts | (a) | (b) |
|---|---|---|
| a combination of A + B | 2% | 5% |
| highly dispersed silicic acid | 1% | 5% |
| talcum | 97% | — |
| kaolin | — | 90% |

Ready-for-use dusts are obtained by intimately mixing the carriers with the combination of active ingredients A+B.

Test Example

Contact action (stomach poison action) against adults of Bemisia tabaci (white flies).

Test Plants

Cotton, 4-leaf stage (circa 20 cm tall).

Test Conditions

Cotton plants kept at 30° C.; 60% relative humidity. Test carried out at 28° C.; 60% relative humidity.

Test Compounds

An Endosulfan of the formula

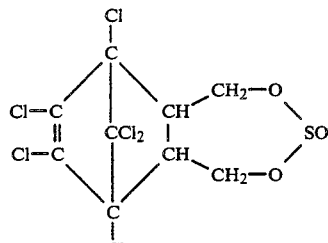

in the form of a 50% emulsifiable concentrate

B Profenofos of the formula

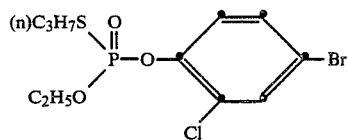

in the form of a 50% emulsifiable concentrate

TEST

Material and methods

The toxicological tests to determine the potentiation between endosulfan and profenofos were carried out using adult white flies which were trapped on infected cotton. Under $CO_2$ anaesthesia, about 50 individuals were put into each of a number of small test cages, the floors of which consisted of a cotton leaf treated with the test solution. Logarithmic gradation of the concentration of the test solutions in which the leaves had been immersed produced gradated mortality values from which, with the aid of the Probit analysis, dosage-mortality lines could be calculated. $2 \times 50$ insects were tested at each of 4 to 5 different concentrations for one dosage-mortality line.

The isobologram in FIG. 1 was established on the basis of the $LC_{50}$ values for both insecticides and an $LC_{50}$ for the mixture thereof in the ratio of their $LC_{50}$ values. On both axes the $LC_{50}$ values are plotted in ppm. The additive activity of the components of the mixture is represented by a straight line intersecting both axes at the 100% point ($=LC_{50}$). Deviation of the empirically found isoboles from the straight line towards the origin of the system signifies potentiation; deviation in the opposite direction signifies antagonism.

As has been proved in numerous experiments, isoboles are symmetric curves and are therefore defined by their intersection points with the axes of the coordinate system and the apex (N) of the curve. In the diagram, the quotient OM/ON is a measure of maximum potentiation ($PR_{max}$). In the present Example, the $LC_{50}$ values for the components of the mixture are: endosulfan 10 ppm (100%) and profenofos 110 ppm (100%). The $LC_{50}$ value for the mixture in the ratio 1:9 is 12 ppm.

Results

The attached diagram shows that the maximum potentiation is $$PR_{max} = OM/ON = 4.6$$

PR values >1 indicate potentiation, PR<1 antagonism. PR=1 signifies additive activity of the components of the mixture, as can be seen from the drawing.

Mathematically, the PR can be obtained from Banki's formula (1978).

$$PR = \frac{\overset{\wedge}{LC_{50}}}{\overset{\bullet}{LC_{50}}} \quad \begin{array}{l}\text{(expected additive effect for the mixture } A + B\text{)} \\ \text{(experimentally found effect for the mixture } A + B\text{)}\end{array}$$

$$\overset{\wedge}{LC_{50}} = \frac{1}{\dfrac{\mu A}{LC_{50}A} + \dfrac{\mu B}{LC_{50}B}} \; ; \begin{array}{l}\mu A \text{ and } \mu B \text{ denote the respective proportions of } A \text{ and } B \text{ in the mixture; } \mu A + \mu B = 1\end{array}$$

Inserting the above $LC_{50}$ values for the insecticides and the mixture thereof in the ratio 1:9 produces an expected $LC_{50}$ of $$\overset{\wedge}{LC_{50}}(1:9) = \frac{1}{\frac{0.1}{10} + \frac{0.9}{110}} = 55$$

$$PR_{max} = \frac{55}{12}$$

$$= 4.58$$

What is claimed is:

1. A pesticidal composition which contains an effective amount of the active component, a combination of 1 part of the compound of the formula

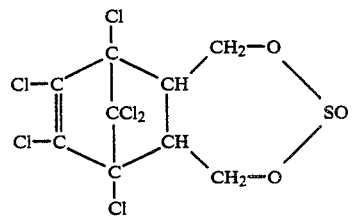

and 9 parts of the compound of the formula

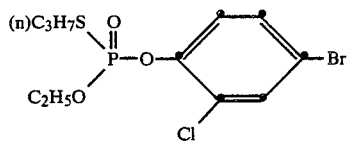

and a carrier.

2. A method of controlling insects and ticks on animals and plants, which method comprises applying to the habitat of said insects and ticks an effective amount of a combination of 1 part of the active compound of the formula

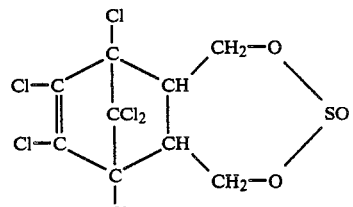

and 9 parts of the active compound of the formula

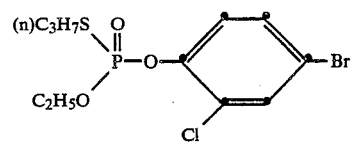

together with a carrier.

3. The method of claim 2, which comprises applying the two active compounds premixed from a single container.

4. The method of claim 2, which comprises applying the two active compounds separately at brief intervals in succession.

5. The method of claim 2, which comprises applying the two active compounds simultaneously from different containers.

* * * * *